United States Patent [19]

Hackl et al.

[11] Patent Number: 5,756,812
[45] Date of Patent: May 26, 1998

[54] PROCESS FOR THE PREPARATION OF PURE (S,S)-N-(1-ETHOXYCARBONYL-3-PHENYLPROPYL) ALANINE

[75] Inventors: Kurt Alfred Hackl; Josef Schaller, both of Linz, Austria

[73] Assignee: DSM Chemie Linz GmbH, Austria

[21] Appl. No.: 795,514

[22] Filed: Feb. 5, 1997

[30] Foreign Application Priority Data

Feb. 5, 1996 [AT] Austria .................................... 199/96

[51] Int. Cl.$^6$ ............................................. C07C 67/52
[52] U.S. Cl. ..................................................... 560/38
[58] Field of Search ......................................... 560/38

[56] References Cited

U.S. PATENT DOCUMENTS 4,542,234  9/1985  Reiley et al. ............................ 560/38

OTHER PUBLICATIONS

Durst, et al., Experimental Organic Chemistry, pp. 70–81, 1980.

*Primary Examiner*—Robert Gerstl
*Attorney, Agent, or Firm*—Wenderoth, Lind & Ponack

[57] ABSTRACT

Process for the preparation of pure (S,S)-N-(1-ethoxycarbonyl-3-phenylpropyl) alanine, in which impure (S,S)-N-(1-ethoxycarbonyl-3-phenylpropyl)alanine is suspended in water, dissolved by heating to the boiling point and separated from insoluble impurities by filtration and the desired end product is then precipitated by cooling, filtered off and dried.

7 Claims, No Drawings

PROCESS FOR THE PREPARATION OF PURE (S,S)-N-(1-ETHOXYCARBONYL-3-PHENYLPROPYL) ALANINE (S,S)-N-(1-Ethoxycarbonyl-3-phenylpropyl)alanine (ECPA) is an essential precursor in the synthesis of various antihypertensive active substances of the angiotensin converting enzyme inhibitor (ACE inhibitor) type, examples being enalapril, enalaprilat, ramipril, delapril etc. The literature already describes several processes for the preparation of ECPA. ECPA is obtained for example by the hydrogenation of (S,S)-N-(1ethoxycarbonyl-3-oxo-3-phenylpropyl) alanine ester (EOPAE). This partial step in the synthesis of ACE inhibitors is already known from the literature, for example from Tetrahedron Letters, vol. 25 (11), pp. 1143–1146, 1984.

Another possible preparation, according to DE-OS 3,542,735, is based on ethyl 2-oxo-4-phenyl-butyrate, which is reacted with L-alanine, in the presence of reducing agents such as sodium cyanoborohydride or hydrogen, and in the presence of a catalyst and a drying agent, in a polar solvent, to give ECPA. Organic Preparations and Procedures Int., 20 (2), 109–115 (1988) has disclosed a third variant, whereby an ethyl ester of alanine is reacted with either tert-butyl 2-bromopropionate or benzyl 2-bromopropionate, in the presence of triethylamine, by refluxing in $CH_3CN$. The resulting ester is then converted to ECPA with HCl/p-dioxane or by catalytic hydrogenolysis with ethanol in the presence of 10% Pd/C.

The problem with these processes, however, is in the isolation of the product and in fact concerns the purity of the ECPA obtained. The crude product, which either precipitates out after the addition of a base or is obtained by extraction, often contains more than 5% by weight of impurities and therefore has to be further purified by crystallization from ethyl acetate, for example as described in the state of the art. However, under the reaction conditions known hitherto, the hydrolysis product (S,S)-N-(1-carboxy-3-phenylpropyl) alanine occurs as a by-product and cannot be removed even by repeated recrystallization from ethyl acetate.

The object of the present invention was accordingly to find an improved process particularly for working up the reaction solutions, which process prevents the formation of the hydrolysis product or makes it possible substantially to remove it from the desired end product.

Unexpectedly, this object could be achieved without the use of an organic extraction agent, by recrystallization from water.

The present invention accordingly provides an improved process for the preparation of pure (S,S)-N-(1-ethoxycarbonyl-3-phenylpropyl) alanine, wherein impure crude (S,S)-N-(1-ethoxycarbonyl-3-phenylpropyl) alanine is suspended in water, dissolved by heating to the boiling point and separated from insoluble impurities by filtration and the desired end product is then precipitated by cooling, filtered off and dried.

The process according to the invention starts from impure crude (S,S)-N-(1-ethoxycarbonyl-3-phenylpropyl) alanine obtained as described in the state of the art. According to the invention, the impure ECPA is suspended in water and dissolved by heating to the boiling point. It is preferably suspended in sufficient water to dissolve all the ECPA. Excessive amounts of water are not recommended as this leads to a greater loss in the recrystallization. The hot solution is then filtered in order to separate off insoluble impurities. The filtrate is then cooled to about 0° to 20° C., preferably 5° to 15° C., with stirring, and the pure ECPA which has precipitated out is filtered off, with or without suction, and dried.

It is preferable to start from a hydrogenation solution obtained for example according to Tetrahedron Letters, vol. 25 (11), pp. 1143–1146, 1984, or according to Example 12 of EP-0,190,687, by the catalytic hydrogenation of EOPAE in acetic acid with the addition of catalytic amounts of sulfuric acid. The desired end product is isolated by first separating off the catalyst and removing the acetic acid solvent by distillation, for example under vacuum on a rotary evaporator. The resulting oily residue is then taken up with water, the amount of water added preferably being such as to give a 40 to 70% solution, particularly preferably a 50 to 60% solution, based on the sulfate contained in the residue. The pH is then adjusted to about 2 to 5, preferably about 3 to 4, by the addition of a base. Suitable bases are preferably sodium hydroxide, potassium hydroxide, sodium or potassium carbonate or sodium or potassium hydrogen carbonate, it also being possible to use mixtures thereof. The resulting solution or suspension is then cooled to about 0° to 20° C., preferably 5° to 15° C., for a period of about 10 to 120 minutes, with stirring, and the product which has precipitated out is filtered off, with or without suction. The ECPA is then suspended in water, as described above, and dissolved by heating to the boiling point. The amount of water can vary here and depends on the amount of ECPA to be dissolved. Again the amount of water used should preferably be sufficient to just dissolve all the ECPA. The hot solution is then filtered to separate off insoluble impurities, analogously to the process described above, for example through a sintered glass suction filter, and the filtrate is then cooled to about 0° to 20° C., preferably 5° to 15° C., with stirring. The ECPA product which has precipitated out is filtered off, with or without suction, and preferably dried in a vacuum drying cabinet at 30° to 50° C., preferably at about 40° C.

The process according to the invention produces ECPA in a yield of over 85% with a purity of up to 99.9%, the proportion of the hydrolysis product (S,S)-N-(1-carboxy-3-phenylpropyl)alanine and the R,S-isomer being less than 0.1% in each case.

EXAMPLE 1

80 g (0.21 mol) of (S,S)-N-(1-ethoxycarbonyl-3-oxo-3-phenylpropyl) alanine benzyl ester were dissolved in 900 ml of acetic acid, and 21.6 g (0.21 mol) of concentrated sulfuric acid were added.

5 pieces of palladium catalyst from Degussa (fixed bed, large) were then added and hydrogenation was carried out for 2 hours at 35° C. and with a circulation rate of 8 l/min until no more $H_2$ was taken up.

Acetic acid was distilled off from the resulting hydrogenation solution under vacuum (about 10 mbar) at 40° C. on a rotary evaporator to give 121.3 g of crude product, which was then diluted with 200 ml of water. 500 ml of 1 N NaOH were then added, bringing the pH to 3.5. The reaction mixture was then ice-cooled to 10° C. for 1 hour, with stirring, and the product which had precipitated out was filtered off with suction. The solid was dissolved in 800 ml of hot water, the solution was filtered hot through a sintered glass suction filter and the filtrate was then ice-cooled to 10° C. for 1 hour, with stirring. The (S,S)-N-(1-ethoxycarbonyl-3-oxo-phenylpropyl)alanine (81.7 g) which had precipitated out was filtered off with suction and dried in a vacuum drying cabinet at 40° C.

Yield: 51.1 g (87.7% of theory)

Melting point: 148.4–148.9° C.

Optical rotation: 24.24° (c=1; MeOH)

HPLC content: 99.88 area %

Hydrolysis product: <0.1 area %

We claim:

1. A process for the preparation of pure (S,S)-N-(1-ethoxycarbonyl-3-phenylpropyl)alanine, wherein impure (S,S)-N-(1-ethoxycarbonyl-3-phenylpropyl)alanine is suspended in water, dissolved by heating to the boiling point and separated from insoluble impurities by filtration and the desired end product is then precipitated by cooling, filtered off and dried.

2. The process as claimed in claim 1 wherein the impure (S,S)-N-(1-ethoxycarbonyl-3-phenylpropyl)alanine is suspended in sufficient water to just dissolve all the (S,S)-N-(1-ethoxycarbonyl-3-phenylpropyl)alanine on heating to the boiling point.

3. A process for the preparation of pure (S,S)-N-(1-ethoxycarbonyl-3-phenylpropyl)alanine wherein, following a catalytic hydrogenation of (S,S)-N-(1-ethoxycarbonyl-3-oxo-3-phenylpropyl)alanine benzyl ester in acetic acid, with the addition of a catalytic amount of sulfuric acids, after the hydrogenation reaction has ended, the acetic acid solvent is removed by distillation, the oily residue is admixed with water and the pH is adjusted to 2 to 5 by the addition of a base, the resulting precipitate of (S,S)-N-(1-ethoxycarbonyl-3-phenylproyl) alanine is then suspended in water, dissolved by heating to the boiling point and separated from insoluble impurities by filtration and the desired end product is then precipitated by cooling, filtered off and dried.

4. The process as claimed in claim 3 wherein the oily residue is taken up with sufficient water to give a 40 to 70% solution, based on the sulfate contained in the residue.

5. The process as claimed in claim 3 wherein the base used is sodium hydroxide, potassium hydroxide, sodium or potassium carbonate or sodium or potassium hydrogen carbonate.

6. The process as claimed in claim 3 wherein the pH is adjusted to 3 to 4.

7. The process as claimed in claim 3 wherein the precipitate of (S,S)-N-(1-ethoxycarbonyl-3-phenylpropyl)alanine obtained after adjustment of the pH to 2 to 5 is suspended in sufficient water to just dissolve all the (S,S)-N-(1-ethoxycarbonyl-3-phenylpropyl)alanine on heating to the boiling point.

\* \* \* \* \*